(12) United States Patent
Weissmahr

(10) Patent No.: US 6,793,886 B1
(45) Date of Patent: Sep. 21, 2004

(54) DEVICE FOR MONITORING FERTILITY IN WOMEN BY OBSERVING PHYSICAL CHANGES IN BODY FLUIDS

(75) Inventor: Joseph A. Weissmahr, Zurich (CH)

(73) Assignee: Kemifar S.R.L., Milan (IT)

( * ) Notice: Subject to any disclaimer, the term of this patent is extended or adjusted under 35 U.S.C. 154(b) by 494 days.

(21) Appl. No.: 09/806,055
(22) PCT Filed: Jul. 25, 2000
(86) PCT No.: PCT/IT00/00314
§ 371 (c)(1), (2), (4) Date: Mar. 30, 2001
(87) PCT Pub. No.: WO01/06932
PCT Pub. Date: Feb. 1, 2001

(30) Foreign Application Priority Data

Jul. 27, 1999 (CH) .............................. 1381/99

(51) Int. Cl.⁷ .............................................. G02B 21/00
(52) U.S. Cl. ...................... 422/61; 422/82.05; 422/99; 600/551; 359/379; 359/381; 359/385; 359/390; 359/398; 359/801; 359/804
(58) Field of Search ............................ 422/61, 82.05, 422/99; 359/801–804, 379, 381, 385, 390, 398; 600/551; 436/906

(56) References Cited

U.S. PATENT DOCUMENTS 3,582,181 A * 6/1971 Manau de Chveca ....... 359/379
4,815,835 A * 3/1989 Ortueta Corona ........... 359/379
4,847,206 A * 7/1989 Heinz ........................... 436/63
5,062,697 A * 11/1991 Mitchell ...................... 359/379
5,267,087 A * 11/1993 Weidemann ................. 359/801
5,572,370 A * 11/1996 Cho ............................ 359/801
5,639,424 A   6/1997 Rausnitz
5,815,311 A * 9/1998 Ishikawa .................... 359/381
5,837,197 A * 11/1998 Porrazzo et al. .............. 422/61
6,052,224 A * 4/2000 Richardson ................. 359/398
6,582,377 B1 * 6/2003 Van Michaels et al. ...... 600/551

FOREIGN PATENT DOCUMENTS

| EP | 528100 | * | 2/1993 |
| JP | 9-54084 | * | 2/1997 |
| WO | 95/28130 | * | 10/1995 |
| WO | 98/19197 | * | 5/1998 |
| WO | WO98/28075 | | 7/1998 |

* cited by examiner

Primary Examiner—Arlen Soderquist
(74) Attorney, Agent, or Firm—Nixon & Vanderhye P.C.

(57) ABSTRACT

A kit (11) is described for the detection of characteristics and parameters of body fluids such as saliva, urine and cervical mucus for the purposes of studying and identifying fertility periods in women, comprising a set of flat plate-shaped supports (3) for samples of said body fluids (F) and a viewer (1) provided with enlargement means, characterized in that each of said flat plate-shape supports (3) for body fluid (F) presents a shallow basin or trap (3p) with a convex bottom entirely surrounded by a raised rim (3r), and is equipped with locking fins (3t) suitable for coupling with structural elements present on said viewer (1) so that it is irreversibly locked onto the latter in a desired relative posititon.

9 Claims, 4 Drawing Sheets

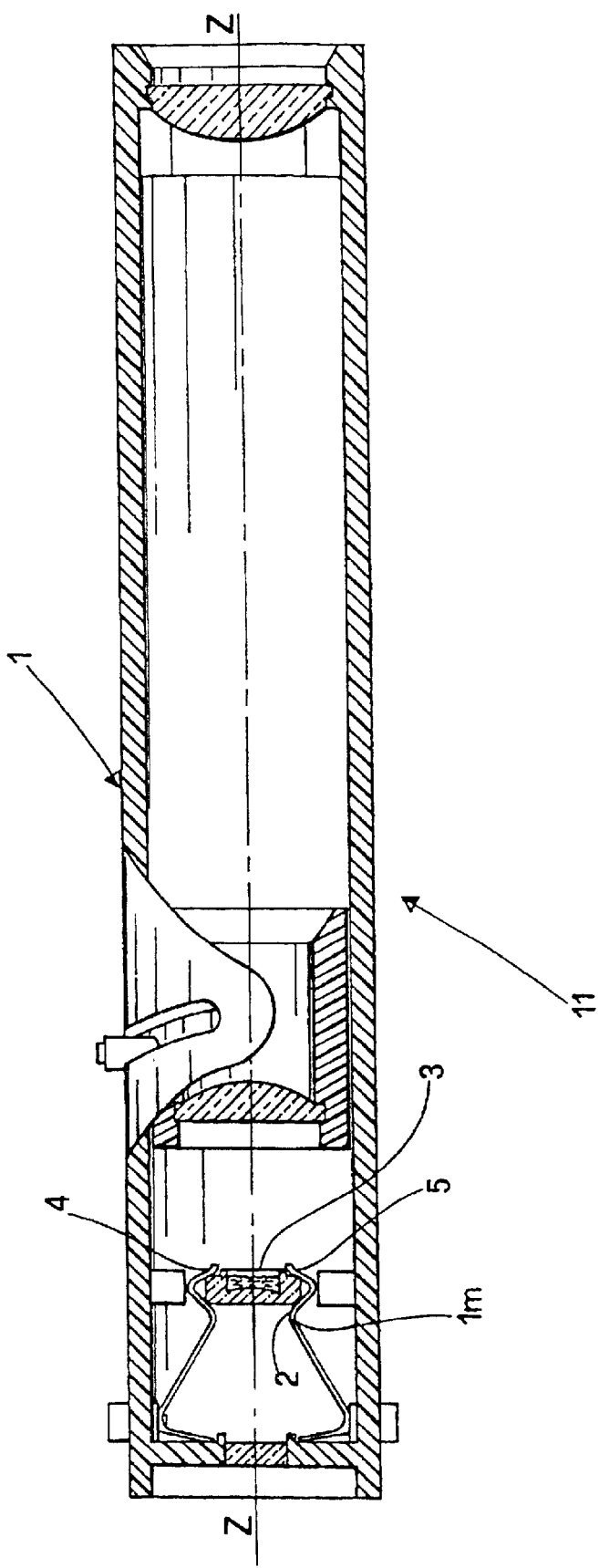

Figure 3:
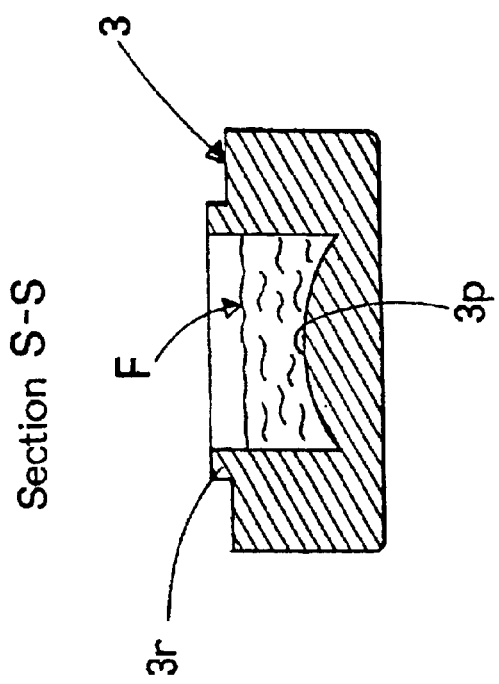

DEVICE FOR MONITORING FERTILITY IN WOMEN BY OBSERVING PHYSICAL CHANGES IN BODY FLUIDS

CROSS-REFERENCE TO PRIORITY APPLICATIONS

This application is the U.S. national phase of international application PCT/IT00/00314 filed Jul. 25, 2000, which designated the U.S., which claims priority from Switzerland Application No. 1381/99 filed Jul. 27, 1999, the contents of which are incorporated herein by reference in their entireties.

The present invention relates to the sector of devices used to obtain and/or improve knowledge of the times of greatest or least "fertility" in women during the monthly menstrual cycle and to identify with a good measure of probability the day when ovulation occurs, for the purposes of contributing to knowledge of the most or least appropriate periods for conception.

More particularly, the present invention relates to a device which proves useful and effective in detecting, by means of a totally natural method and without the use of either chemicals or "invasive" procedures, the fertile days and the time of ovulation in women with a very high degree of approximation (such as to allow various applications both in the field of physiological events and in that of medical intervention).

The invention relates essentially to a detection system for assessing information closely related to changes of a physical type in a number of body fluids which can be collected without invasive measures, such as saliva and other fluids which will be specified here below.

In the light of the present state of our technical and scientific knowledge, it is known that, in the course of the menstrual cycle, important, essentially hormone-based physiological transformations take place in the woman for the purposes of optimising the conditions for possible conception. Since this "natural" program has a very strong functional purpose, it comes about that various biological variables related to it, despite the "biological variability" which is always present, take on a character and values which tend to be deterministic and leave little room for chance.

These variables are numerous and different in nature, such as hormone levels, body temperatures, density and viscosity of certain fluids, i.a. As the days of the cycle leading up to the time of ovulation and then following ovulation pass, these variables change in value and thus reflect actual physical changes in a number of elements of the body.

It is also well known that the woman's fertile period occurs only once in the course of each menstrual cycle. The ovum matures around mid-cycle, roughly 14 days after the start of the last menstruation. The fertility period, i.e. the days when the ovum can be fertilised, covers a maximum of 5–6 days (with a greater chance of fertilisation on the 2–3 central days of the period).

Identification of this short period of "maximum fertility" is not easy, unless sophisticated, expensive and sometimes also "invasive" methods are used. The various traditional methods based on calculations and subjective observations are very imprecise and not always easy to use. All this often leads to practical consequences of substantial distress in couples that desire to conceive a child or who would like to implement proper family planning on the basis of wholly natural methods. In recent years, then, substantial efforts have been made in an attempt to develop reliable, easy-to-use predictive tests, based on changes in the above-mentioned biological variables which mark the various phases of the cycle in the woman.

One variable often used for this purpose is basal temperature, which, as is known, tends to rise at the time of ovulation. The use of this variable, which can easily be measured with special ad-hoc thermometers, yields information which is sometimes not particularly accurate and is often influenced by other factors.

Another variable considered is the viscosity (either subjectively assessed or measured using an instrument called a viscosimeter) of the uterine cervical mucus, which is not always easy to assess.

All these variables, moreover, require evaluation not only of the "present" value, but also of the variations compared to the last few days. Their reliability in practical use has therefore often proved fairly poor.

One very reliable variable which is less influenced by other factors is the luteinising hormone (LH) level in the female body. It can be measured precisely with sophisticated laboratory equipment and, more recently, with the introduction of special kits on the market, it can also be measured at home; these kits are quite expensive and, for reliable conclusions regarding fertility, again require comparison with results obtained on a number of consecutive days.

Lastly, we should recall that comparative tests performed by authoritative investigators have shown and confirmed that, during the menstrual cycle, the woman's saliva (or other fluids such as cervical mucus) undergoes structural changes as a result of the oestrogen levels circulating in the body; as a result, over a period ranging from 2–3 days before ovulation (oestrogen peak) to 2–3 days after ovulation, a physical phenomenon of microscopic "crystallisation" of saliva occurs, which, in turn, can be recognised and, if properly interpreted, used to understand which phase of the cycle the woman is in from the fertility point of view.

The above-mentioned observations are summarised in the following specification which also allows comparison with the information that the woman can obtain using the various "natural" methods outlined above.

In the light of the present state of our technical and scientific knowledge, it can be stated that this latter effect of crystallisation of saliva, known as the "fern effect", in that the crystals present the appearance of the fronds of a fern, has been used in laboratories and in specialist medical studies in order to "see" the crystalline structure indicating a pre- or post-ovulation condition under the microscope, thus allowing conclusions to be drawn as to the woman's fertility status. Small microscopes for personal use have also been produced for said purpose.

The above-mentioned approach also affords advantages particularly when used in conjunction with other natural methods, but it also presents a number of drawbacks related mainly to the need to perform calculations and take account of the results of previous days, as well as a certain amount of objective difficulty in collecting samples of saliva (which prove hard to compare) in a simple, standardised manner over time.

The object of the present invention is a device suitable for detecting changes in the "state" of fluids, such as saliva, in response to a rapid increase in oestrogen levels in the body and other changes closely linked to the approach and occurrence of the physiological phenomenon of ovulation (which, as already mentioned, is a phenomenon with an intense deterministic component, that strongly influences the changes observed).

More particularly, the object of the present invention is a kit as described in the preamble of claim 1 attached hereto, characterised in the characterising clause of the same claim.

The present invention makes it possible to overcome the various limitations of the above-mentioned systems (difficulty in collecting standardised samples of saliva or other fluids; poor sensitivity related to visual observation of saliva placed on surfaces with undefined limits, such as slides, lenses or the like; the need to save the results of preceding days with the difficulty of detecting the onset of changes which are not particularly marked as compared to previous findings).

In fact, the object of the present invention consists in a kit made up of:

- a device for collecting and storing samples consisting of a set of flat plate-shaped supports (hereinafter called "petals") made of special material, as specified here below, with an entirely original design which enables the fluid samples (saliva or other fluids) to be collected in a homogenous, standardised manner by implementing a kind of automatic mechanism as will be explained later in this description. Said set of petals makes it possible to obtain: greater reliability of results due to the standardised collection of fluid in constant amounts; greater sensitivity due both to the quality of the sample and to the way the petal is constructed, with the possibility of easy comparison with the results of groups of subsequent days with immediate detection of any changes and with the further possibility of saving indefinitely the effective results ("values" of the variables used, with the consequent possibility of comparing them over time with later cycles, checks, interpolations and extrapolations);
- a petal readout device consisting in a viewer of appropriate shape, as described here below, in which the petals can be inserted for the purposes of the optical or electrical or mixed optical-electrical detection of the crystallisation of saliva or other fluids. The mixed system may substantially enhance the sensitivity of the device with only a slight increase in cost, inasmuch as the electrical component can be realised at only limited extra expense.

Figure 2:
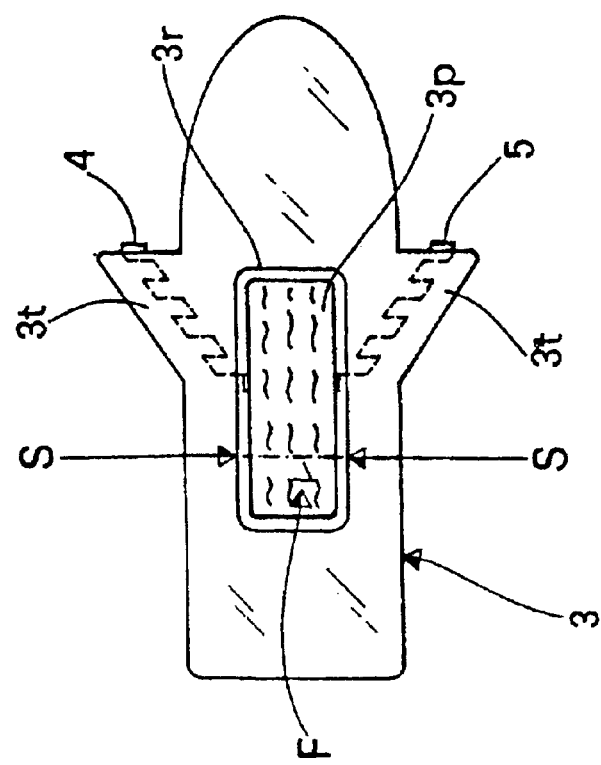
Figure 4:
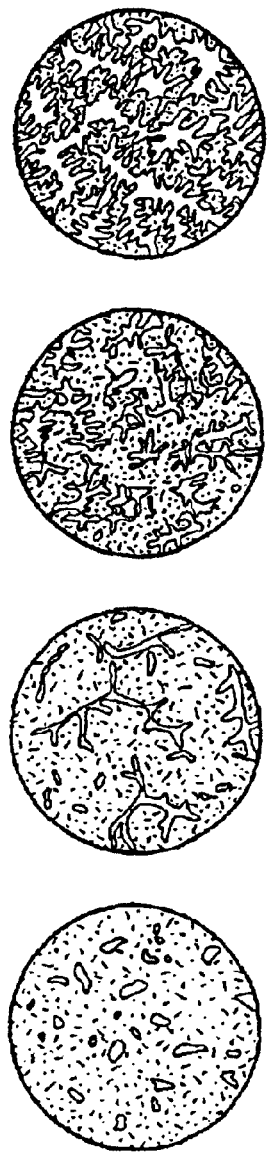
Figure 5:
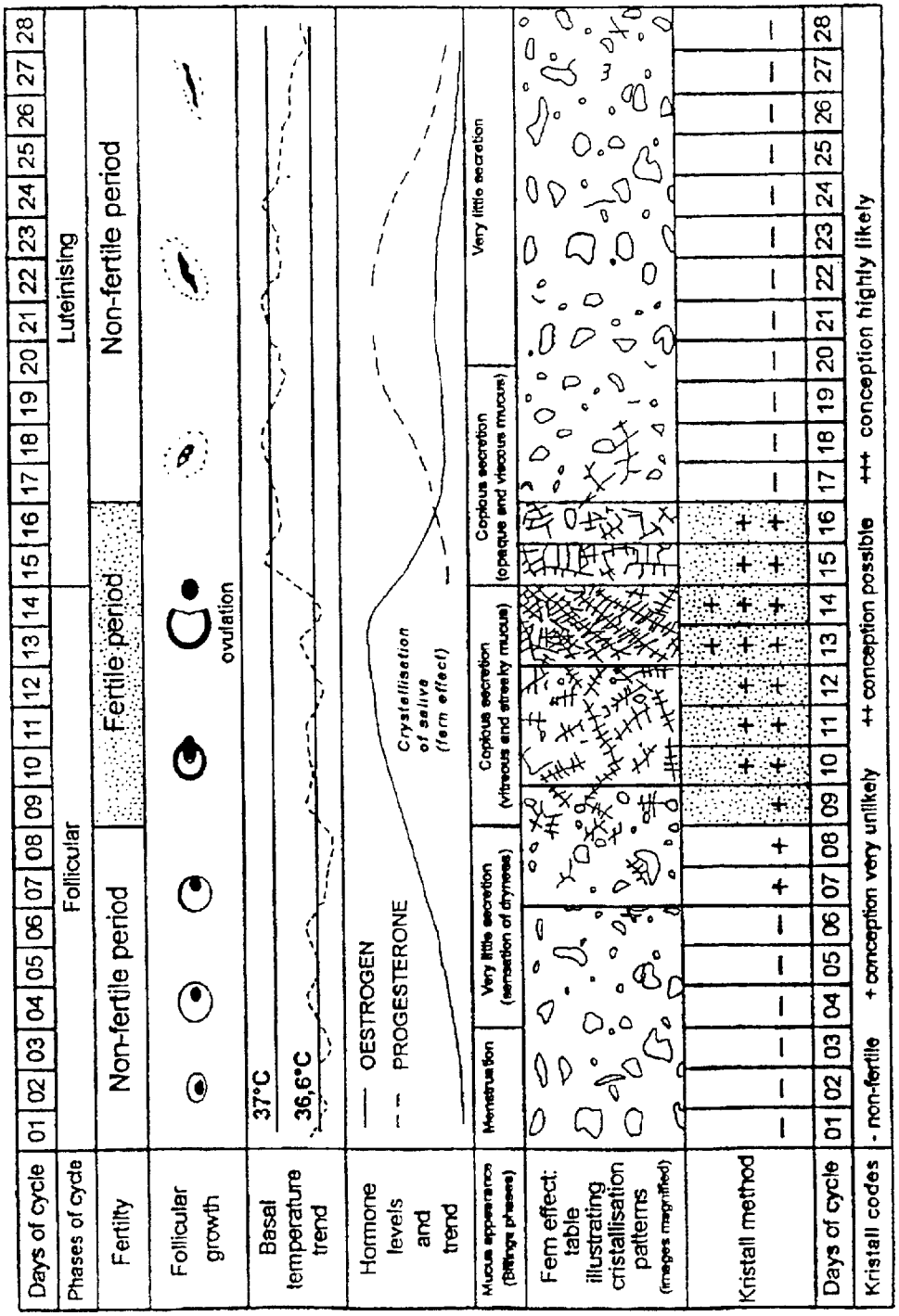

A preferred embodiment of the kit according to the invention will be described in greater detail here below, making reference to the attached drawings which represent:

in FIG. 1, the longitudinal section of a viewer according to the invention in which a flat plate-shaped support (or "petal") is inserted for physiological fluid samples;

in FIG. 2, the plan view of one of said petals according to the invention;

in FIG. 3, the cross sectional view of the same petal;

in FIG. 4, a sequence of images obtained optically with the viewer in FIG. 1, showing an example of successive changes in the image over a period concluding with ovulation; and in FIG. 5, a graph showing the trend of the ovulation phase during the menstrual cycle of a woman.

As shown in FIG. 1, the viewer 1 equipped with flat-convex lenses and other features which are well known in the field of optical instruments presents a compartment 2, perpendicular to the Z-Z optical axis of viewer 1, suitable for housing a flat plate-shaped support (see also FIGS. 2 and 3) carrying a sample of physiological fluid F. This flat plate-shaped support, or petal 3, is obtained from special high-transparency synthetic material (preferably high-transparency polystyrene) and presents a shallow basin or trap 3p with a slightly convex bottom entirely surrounded by a raised rim 3r. As a result of the surface tensions exerted by the raised rim, a sample of physiological fluid F deposited in said shallow basin necessarily takes on a fixed conformation depending on the geometry of the system, with a flat part of predetermined thickness positioned at the centre of the visual field of viewer 1.

A spring clip 1m holds petal 3 in a fixed position after its insertion in compartment 2, while two projecting sidepieces, in the form of the two fins 3t, act as end-stops or locking elements in contact with the outer edges of said compartment 2.

This enables petal 3 to be positioned consistently in the same position in relation to the viewer in which it is inserted, which is a very important feature for reliable standardisation of the method in terms of readouts of results and their comparison.

The system produced presents undoubted advantages compared to previous systems and allows any woman to carry out the simple, inexpensive and continuous monitoring of her fertility status with very precise identification of the time of ovulation.

The multi-petal system (a complete set contains 32 petals with a container, not illustrated here, for their collection) allows sample collection and thus the monitoring of the history of an entire cycle (or even of several cycles), enabling the woman to trace the changes in the state of crystallisation of saliva which constitute the real marker showing when ovulation is imminent.

The sequence of images presented in FIG. 4, detected optically using the above-mentioned viewer provides an example of these variations in a "typical" cycle over a period culminating in ovulation.

It will easily be understood that the effective information content lies in detection of the changes, since a certain amount of "random noise" will always be present in any single "current" image. It is well known, in fact, that the human sensory system is much more capable of detecting changes in an image than its specific descriptive content.

It is also very important to achieve a kind of "automation" in the distribution of the saliva collected on the surface of the petal. This has been achieved, as mentioned above, by producing the central saliva trap 2 with a specially designed profile which exploits the surface tension and causes the saliva deposited in the trap to spread regularly and consistently in a uniform manner inside the trap, with a flat area located at the centre of the visual field of the viewer.

The elements listed here above constitute the original features of the multi-petal system according to the invention. Viewer 1 is specially designed to receive the petals and detect the crystallisation patterns of saliva or other fluids basically by means of optical readout, but also, as we shall see here below, with the additional possibility of obtaining confirmation by the quantitative assessment of an electrical magnitude consisting in a conductivity parameter for the saliva contained in the petal, the value of which may change appreciably and rapidly when a phenomenon of microcrystallisation of the saliva occurs. This dual ability to detect changes related to crystallisation (with a consequent significant increase in the sensitivity of the method) constitutes an additional original feature of the kit, to which should be added the original mode of inserting, centring and locking petal 3, which thus remains optimally positioned for the optical readout.

Kit 11 comprises a container (not illustrated) for the collection of a set of 32 petals, all produced with technical material characteristics specified for each production batch, such as to guarantee a percentage of impurities which is below the predetermined threshold.

Said container can be of the known multi-pocket type and made of soft material.

As already mentioned, for the assessment of the electrical parameters of physiological fluids such as saliva, urine, cervical mucus, etc., a sample of which has been deposited on petal 3, the inventor of the present invention has provided for the application, on both sides of each petal 3, preferably at the level of said locking fins 3t, of two inserts 4 and 5, made of conductive material, with one end in contact with fluid F. These inserts 4 and 5 can be connected up to a voltage generator and the electrical magnitude of the current passed through fluid F can be measured and assessed for the purposes of identifying the corresponding potential fertility level.

The kit which is the object of the present invention allows maximum detection of changes in the physical state of the biological fluid (saliva or other fluid) for numerous applications which are inexpensive and easy to implement by means of the kit.

The use of the kit presents no difficulties and can be managed by the woman concerned without the aid of her doctor. However, it also makes for an invaluable exchange of information between doctor and patient in the context of various physiological or clinical problems. The use of the system can be summarised in the following operations.

The saliva is collected on a finger which has been washed to eliminate all impurities (the woman must avoid collecting saliva immediately after consuming food or appreciable amounts of alcohol, or after smoking a substantial number of cigarettes). The same procedures are adopted for the collection of cervical mucus.

The saliva is transferred to saliva trap 3p at the centre of petal 3, eliminating any excess air bubbles.

The saliva is left to dry for a few minutes (once dried, the sample conserves its inner crystallization for a longer period). To eliminate it, all that is necessary is to rinse it in warm water.

The petal is inserted in compartment 2 where it is held by spring clip 1m and is then pushed right in to the end-stop position so that the fins 3t touch the inserts 3n. With the petal locked in this position, the crystallised saliva is optimally placed in the optical detection field (and, if the electrical measurement option is implemented, it will be in the correct position for connecting up to a device known to be suitable for such measurements, which may take the form of a battery-operated mini-calculator with a liquid crystal display for the readout of saliva conductivity values).

One then proceeds with the direct visual readout, which enables the woman to observe and assess the image which, according to the phase of the menstrual cycle, will resemble one of the four images illustrated in FIG. 4. Obviously, these images can also be collected photographically or "digitised" by means of a suitable electronic interface with the possibility of easy subsequent recall, without having to reinsert the petal, for the purpose of comparing results on different days.

The petals can be numbered and stored in a special container with labels so as to be able to easily identify the results for any given day and repeat comparisons as many times as one wishes.

The main applications for which the system described here above can be used and for which the system has been successfully tried are the following.

Identification of the Day of Ovulation

This application is implemented by detecting the crystallisation image every day after the start of the menstrual period until such time as the image is seen to pass from type 3 to type 4 (FIG. 4). The finding is also confirmed by the fact that on the following days the image will revert to type 3. The days straddling the time of identification of the day of ovulation constitute the ideal time for conception.

Monitoring of Fertile Periods

The daily collection of samples and the day-by-day comparison of petals makes it possible to check the changes in image from type 1 and/or type 2 to type 3 and ultimately to type 4. The time at which this transition occurs may be regarded as the start of the fertile period which will continue after ovulation until the image changes back to types 2 and 1.

Control of Pre-menopause Irregular Cycles

This application is implemented by testing the samples every day and observing all the petals after completing sample collection so as to establish whether the crystallisation occurs in a regular manner (using + or − to indicate early or late crystallisation, as the case may be), as, for instance, illustrated schematically in FIG. 4. If crystallisation does not occur at any time in one or more cycles, this will be a clear indicator of a hormone abnormality which the specialist will need to investigate.

Estimate of the Probable Sex of the Newborn at Conception

Various researchers have shown that the sex of the foetus is determined by the type of spermatozoon that fertilises the ovum. Spermatozoa carrying male or female sexual chromosomes have different survival times. The result is that if conception occurs early (shortly after ovulation) there is a greater likelihood that it will be produced by "female"-type spermatozoa, whereas, if conception occurs later in relation to ovulation it is more likely to have been produced by "male"-type spermatozoa.

The system produced with the kit of the present invention consists in taking several readouts a day starting from the time the image passes from type 2 to type 3, i.e. in order to identify exactly the time of day when it passes from type 3 to type 4. This observation may allow estimation of the time of ovulation to within approximately 12 hours. This information in turn allows the couple to implement behaviour strategies which will help to avoid conception in the time range when the more "desired" sex is less likely.

FIG. 5 presents a graph, based on readouts obtained with a kit according to the present invention, showing the trend of the ovulation phase during the woman's menstrual cycle.

Given here below is a summary of the results of a number of "controlled" tests performed using the method described above in some of its possible applications.

Research Comparing Various Methods for Determining the Day of Ovulation (Ukraine)

Aim of the research:

identifying the ovulation phase comparing the saliva cystallisation method with various other "physiological" methods (cervical mucus testing, basal temperature, pupil measurement, oestrogen assay) in a group of about 500 women.

| | |
|---|---|
| Country | Ukraine |
| Date of study | 1993–94 |
| N. of researchers | 8 |
| N. of women | 514 (aged 15–46) |
| Cycles observed | 5,498 (mean:10.7) |
| Dropouts | 42 (8.2%) |
| Results: | |
| | |
| Crystallisation[1] | 428 (91%) |
| Cervical mucus[2] | 398 (84%) |
| Pupil measurement[3] | 364 (77%) |
| Oestrogen assay [[(4)]] | 472 (100%) |

[1]Cases in which the fertile phase (ovulation period) was detected by crystallisation of saliva, coinciding with oestrogen levels[[(4)]] in the appropriate range: peak value ± 10%.
[2]Detection of the fertile phase according to the Billings Method, as checked by estrogen levels[[(4)]]: peak value ± 15%.
[3]Detection of pupil dilatation, as checked by oestrogen values[[(4)]]: peak value ± 10%.

Research Comparing Various Methods for Determining the Day of Ovulation (Czech Republic)

Aim of the research:

identifying the ovulation phase comparing the monitoring of crystallisation of saliva with three other methods (folliculometry, basal temperature, hormone test) in a group of 48 women observed for a period of 5 months.

| | |
|---|---|
| Country | Czech Republic |
| Date of study | 1992 |
| N. of researchers | 2 |
| N. of women | 48 (aged 16–45) |
| Cycles observed | 5 |
| Dropouts | 0 |
| Results: | |
| | |
| Crystallisation[1] | 48 (100%) |
| | Correlation: 100% |
| Folliculometry[1] | 48 (100%) |
| Basal temperature[2] | 36 (75%) |
| Hormone test[3] | 48 (100%) |

[1]Cases in which the ovulation phase was precisely identified by crystallisation of saliva, coinciding perfectly with folliculometry results.
[2]Cases in which a rise in temperature of at least 0.2° C. was detected corresponding to the ovulation phase as detected by folliculometry.
[3]Tested by hormone assay.

The data shown demonstrate the excellent application capability of the method described above for obtaining reliable results of practical utility.

What is claimed is:

1. A kit for the detection of characteristics and parameters of body fluids such as saliva, urine and cervical mucus for the purpose of studying and identifying fertility periods in women, comprising a set of flat plate-shaped supports for samples of body fluids and a viewer provided with structural elements and an enlargement device, wherein each of said flat plate-shaped supports for the body fluid comprises a shallow basin or trap with a convex bottom entirely surrounded by a raised rim and is equipped with one or more locking fins suitable for coupling with the structural elements of said viewer so that it is irreversibly locked onto the latter in a desired relative position.

2. The kit according to claim 1, wherein each of said projecting fins acts as an end-stop in contact with an outer edge of a compartment in said viewer which is suitable for containing it.

3. The kit according to anyone of the preceding claims, further comprising a tension generator device, wherein at least two inserts made of conductive material are fitted on either side of said flat plate-shaped supports for samples of body fluid for connection to the poles of said tension generator in order to measure electrical-type magnitudes of a current passing through said body fluid.

4. The kit according to claim 3, wherein said flat plate-shaped supports for samples of body fluid are made of high-transparency polystyrene.

5. The kit according to claim 3, further comprising a set of several flat plate-shaped supports and a suitable container for said supports.

6. The kit according to claim 3, wherein said flat plate-shaped supports making up a set are 32 in number.

7. The kit according to anyone of the claim 1 or 2, wherein said flat plate-shaped supports for samples of body fluid are made of high-transparency polystyrene.

8. The kit according to anyone of the claim 1 or 2, further comprising a set of several flat plate-shaped supports and a suitable container for said supports.

9. The kit according to anyone of claim 1 or 2, wherein said flat plate-shaped supports making up a set are 32 in number.

\* \* \* \* \*